United States Patent [19]
Taylor et al.

[11] Patent Number: 5,098,396
[45] Date of Patent: Mar. 24, 1992

[54] VALVE FOR AN INTRAVASCULAR CATHETER DEVICE

[76] Inventors: Ellis R. Taylor, 17 Portland Pl., St. Louis, Mo. 63108; Robert Case, 56 West Schiller, Chicago, Ill. 60610; James D. Morrow, 718 North Elmwood, Oak Park, Ill. 60302

[21] Appl. No.: 600,432

[22] Filed: Oct. 19, 1990

[51] Int. Cl.$^5$ .............................. A61M 5/00
[52] U.S. Cl. .................. 604/169; 604/246; 604/250; 251/7
[58] Field of Search ............. 604/164, 169, 181, 186, 604/246, 250, 256; 251/7, 149.1

[56] References Cited

U.S. PATENT DOCUMENTS

| | | | |
|---|---|---|---|
| 3,769,975 | 11/1973 | Nimoy et al. | 128/214 |
| 4,006,744 | 2/1977 | Steer | 128/214 |
| 4,192,304 | 3/1980 | Millet | 128/214 |
| 4,243,034 | 1/1981 | Brandt | 604/169 |
| 4,360,024 | 11/1982 | Wallace | 604/256 |
| 4,397,442 | 8/1983 | Larkin | 251/342 |
| 4,409,991 | 10/1983 | Eldridge | 128/766 |
| 4,429,852 | 2/1984 | Tersteegen et al. | 251/9 |
| 4,453,295 | 6/1984 | Laszczower | 251/10 |
| 4,560,378 | 12/1985 | Weiland | 604/83 |
| 4,570,898 | 2/1986 | Staeubli | 251/4 |
| 4,643,389 | 2/1987 | Elson et al. | 251/10 |
| 4,673,161 | 6/1987 | Flynn et al. | 251/10 |
| 4,795,430 | 1/1989 | Quinn et al. | 604/97 |
| 4,802,650 | 2/1989 | Stricker | 251/117 |
| 4,834,712 | 5/1989 | Quinn et al. | 604/175 |
| 4,900,306 | 2/1990 | Quinn et al. | 604/97 |

FOREIGN PATENT DOCUMENTS 3324699 12/1984 Fed. Rep. of Germany ...... 604/250

Primary Examiner—John D. Yasko
Assistant Examiner—Corrine Maglione
Attorney, Agent, or Firm—Wallenstein, Wagner & Hattis

[57] ABSTRACT

An intravascular catheter device that serves to control the loss of blood and subsequent contamination of the operator during placement, is disclosed. The catheter device comprises a cannula, a hub, and a generally cylindrical, resilient valve disposed within the hub. The valve includes an inner surface and an outer surface. The inner surface defines a passage in fluid communication with the cannula and has a plurality of longitudinal inner surface ribs. The outer surface has a plurality of outer surface ribs which are radially aligned with a respective one of the inner surface ribs. The catheter device further includes a ring for selectively compressing the outer surface ribs a distance to bring the inner surface ribs into mutual contact.

8 Claims, 1 Drawing Sheet

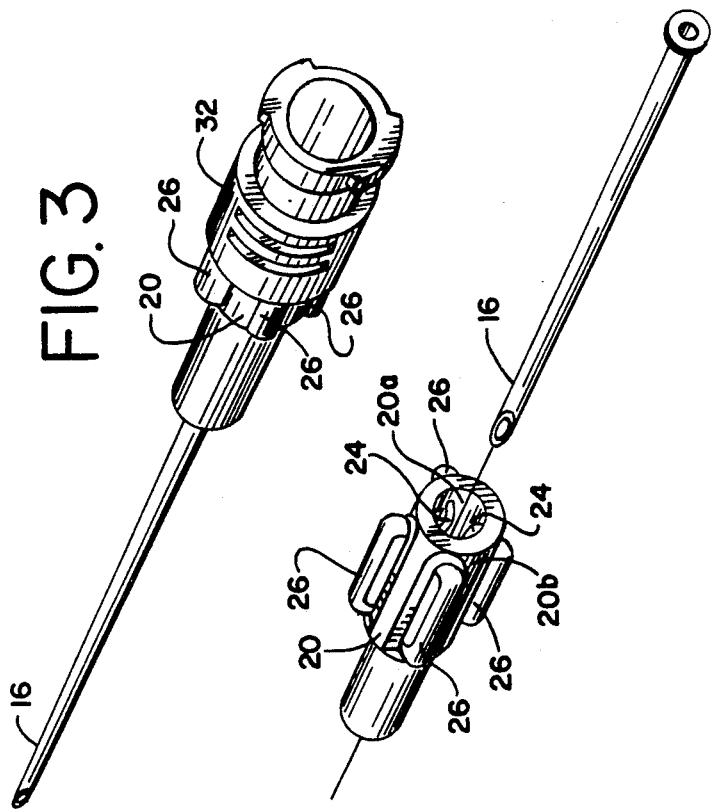
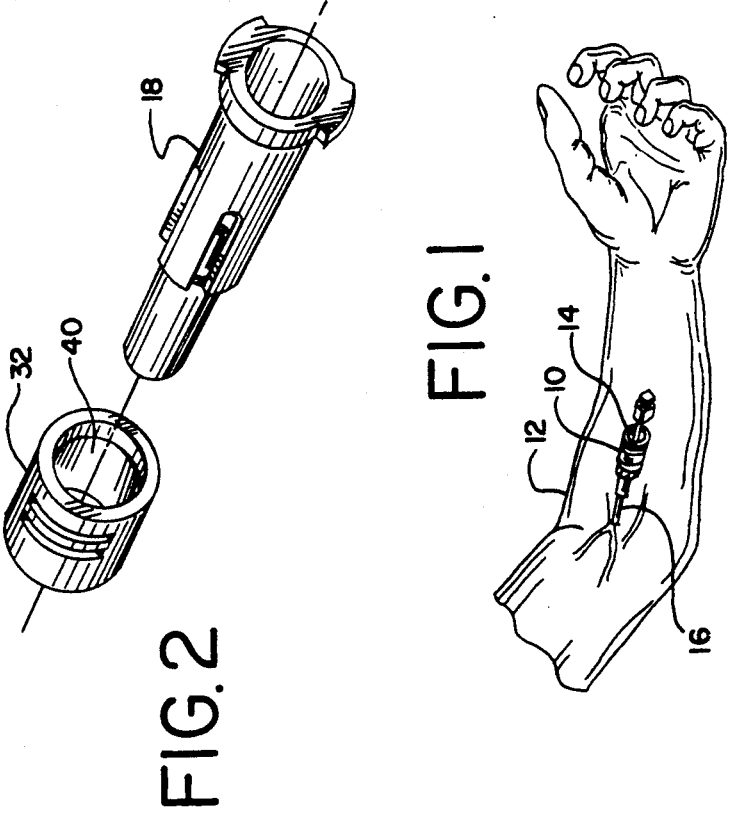

VALVE FOR AN INTRAVASCULAR CATHETER DEVICE

DESCRIPTION

1. Technical Field

Applicants invention relates to intravascular catheter devices and, more particularly, to a flow control device for preventing back flow of blood.

2. Background of the Invention

Intravascular catheters are typically inserted into a vein or artery of a patient in order to administer drugs or fluid to a patient. When inserted into a vein or artery, intravascular catheters can permit blood to flow back through the catheter under its own pressure. As discussed in U.S. Pat. No. 4,360,024 to Wallace, entitled "Catheter With Liquid Flow Control Means", in certain circumstances this flow-back of blood is undesirable. Particularly if uncontrolled, this back flow and subsequent leaking of blood is inconvenient and even, in some cases, hazardous due to possible contamination of the operator and/or consequent infection of the patient.

A common procedure used to introduce a plastic catheter is to include a sharp hollow needle, or trocar, within a bore of the catheter. This needle acts as a sharp introducer over which the catheter can be advanced into the blood vessel. When the needle is inserted, blood flows rapidly back through the catheter but is easily controlled at its proximal end. However, a problem arises when the needle is withdrawn through the bore of the catheter, thus allowing blood to flow freely through the catheter until the catheter is connected to other equipment incorporating a control device for the blood flow. This free flow of blood prior to connecting the catheter to the equipment provides a dangerous risk of contamination of the operator.

Wallace discloses a catheter having a hub portion and a bore through the hub portion. The hub portion is described as resiliently distortable to close the bore by manual pressure. Particularly, the hub portion comprises portions adapted to be gripped between a finger and thumb of the operator to close the bore. However, the hub portion must be completely collapsed to prevent back-flow. Additionally, pressure on the hub portion must be continuously maintained by the operator to continuously prevent back-flow.

Applicants' invention is provided to solve these and other problems.

SUMMARY OF THE INVENTION

It is an object of the invention to provide an intravascular catheter device that eliminates the free flow of blood from the catheter device upon removal of the needle, thereby minimizing the risk of contamination of the operator.

In accordance with the invention, the catheter device comprises a cannula, a hub, and a generally cylindrical, resilient valve disposed within the hub. The valve includes an inner surface and an outer surface. The inner surface defines a passage in fluid communication with the cannula and has a plurality of longitudinal inner surface ribs. The outer surface has a plurality of outer surface ribs which are radially aligned with respective ones of the inner surface ribs.

The catheter device further includes means for selectively compressing the outer surface ribs a sufficient distance to bring the inner surface ribs into mutual contact. It is contemplated that the compressing means comprises a ring.

It is further contemplated that the intravascular catheter device includes means for selectively maintaining the valve in either of a closed position, wherein the inner surface ribs are in contact, and an open position wherein the inner surface ribs are not in contact.

It is still further contemplated that the maintaining means comprises an annular detent radially disposed on the ring, and spaced first and second collar tabs on the hub. The tabs selectively alternately receive the annular detent.

Finally, it is contemplated that there are four inner and outer surface ribs equally circumferentially spaced about the valve.

Other features and advantages of the invention will be apparent from the following specification taken in conjunction with the following drawings.

BRIEF DESCRIPTION OF DRAWINGS

FIG. 1 is a perspective view of a catheter device inserted into a forearm;

FIG. 2 is an exploded perspective view of a catheter device according to the invention;

FIG. 3 is an assembled perspective view of the catheter device of FIG. 2;

FIG. 4 is a sectional view of the catheter device of FIG. 2 with the valve in the open position; and FIG. 5 is a sectional view of the catheter device of FIG. 2 with the valve in the closed position.

DESCRIPTION OF THE PREFERRED EMBODIMENT

While this invention is susceptible of embodiments in many different forms, there is shown in the drawings and will herein be described in detail, a preferred embodiment of the invention with the understanding that the present disclosure is to be considered as an exemplification of the principles of the invention and is not intended to limit the broad aspects of the invention to the particular embodiment illustrated.

An intravascular catheter device 10 according to the invention is illustrated in FIG. 1 inserted into a forearm 12 of a patient. As is well known, the catheter device 10 includes a needle 14 for facilitating insertion of a cannula 16 below the skin of the patient.

The catheter device 10 is illustrated in greater detail in FIGS. 2 and 3. The catheter device 10 includes a hub 18 and a generally cylindrical, resilient valve 20 disposed within the hub 18. It is contemplated that the valve 20 is formed of a material such as a thermoplastic elastomer. The valve 20 includes an inner surface 20a and an outer surface 20b. The inner surface 20a defines a passage in fluid communication with the cannula 16 and has four circumferentially spaced longitudinal inner surface ribs 24. The outer surface 20b has four outer surface ribs 26. Each of the outer surface ribs 26 is radially aligned with a respective one of the inner surface ribs 24. The inner and the outer surface ribs 24, 26, are equally spaced about circumferentially of the valve 20.

The catheter device 10 further includes a ring 32 having a taper 33 (FIGS. 4 and 5). The ring 32 is slidable over the valve 20 between an open and a closed position. As the ring is moved to the closed position, the taper 33 of the ring 32 compresses the four outer surface ribs 26 a sufficient distance to bring the inner surface ribs 24 into mutual contact, thereby preventing flow of fluid through the valve 20, thus preventing back flow of blood. As the ring 18 is moved to the open position, the taper 33 is moved away from the outer surface ribs 26, permitting the resilient valve 20 to expand, thereby pulling the inner surface ribs 24 away from one another, thus permitting fluid to flow therethrough. Because of the gradual slope of the taper 33, effectively an infinite consistent control of the rate of blood flow is provided. Further, the ring 18 tends to remain in a set position, so that once a desired rate of flow is selected, the operator's hand may be removed from the ring to perform other tasks.

The catheter device 10 is illustrated in cross section in FIG. 4 in the open position and in FIG. 5 in the closed position.

Particularly, as illustrated in FIG. 5, when the valve 20 is in the closed position, the outer surface ribs 26 are compressed by the taper 33 of the ring 32, compressing the inner surface ribs 24 to mutual contact. As illustrated in FIG. 4, when the valve 20 is in the open position, the taper 33 of the valve 32 is removed from the outer surface ribs 33 of the ring 32, and, accordingly, the inner surface ribs 24 are not in contact.

In order to maintain the valve 20 in either of the open or the closed positions so that both of the operator's hands are free to perform other tasks, an annular detent 40 radially disposed about the inner surface of the ring 32 is provided. Additionally, spaced first and second collar tabs 42, 44, respectively, are provided on the hub 18. The first and second collar tabs selectively alternately receive the annular detent 40

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

We claim:

1. An intravascular catheter device comprising:
   a cannula having a proximal end and distal end;
   a hub;
   means disposed within said hub for selectively controlling flow of fluid through said cannula, said controlling means including an inner surface and an outer surface, said inner surface defining a passage in fluid communication with said cannula and having a plurality of inner surface ribs, said outer surface having a plurality of outer surface ribs, said outer surface ribs aligned with a respective one of said inner surface ribs; and
   means found on said hub for selectively compressing said outer surface ribs a distance to bring said inner surface ribs into mutual contact.

2. A device for selectively controlling fluid flow through a cannula of an intravascular catheter, said device comprising:
   a hub attached to said cannula;
   a generally cylindrical, resilient valve disposed within said hub, the valve including an inner surface and an outer surface, said inner surface defining a passage in fluid communication with said cannula and having a plurality of longitudinal inner surface ribs, said outer surface having a plurality of outer surface ribs, said outer surface ribs radially aligned with a respective one of said inner surface ribs; and
   means found on said hub for selectively compressing said outer surface ribs a distance to bring said inner surface ribs into mutual contact.

3. An intravascular catheter device comprising:
   a cannula having a proximal end and a distal end;
   a hub attached to the proximal end of said cannula;
   a generally cylindrical, resilient valve disposed within said hub, said valve including an inner surface and an outer surface, said inner surface defining a passage in fluid communication with said cannula and having a plurality of longitudinal inner surface ribs, said outer surface having a plurality of outer surface ribs, said outer surface ribs radially aligned with a respective one of said inner surface ribs; and
   means found on said hub for selectively compressing said outer surface ribs a sufficient distance to bring said inner surface ribs into mutual contact.

4. The intravascular catheter device of claim 3 wherein said compressing means comprises a ring.

5. The intravascular catheter device of claim 4 further including means associated with said hub and said ring for selectively maintaining said valve in either of a closed position, wherein said inner surface ribs are in contact, and an open position, wherein said inner surface ribs are not in contact.

6. The intravascular catheter device of claim 5 wherein said maintaining means comprises an annular detent radially disposed on said ring and spaced first and second collar tabs on said hub, said tabs for selectively alternately receiving said annular detent.

7. The intravascular catheter device of claim 3 wherein said inner and outer surface ribs are equally spaced about said valve.

8. The intravascular catheter device of claim 3 including four inner and four outer surface ribs equally spaced about said valve.

* * * * *

UNITED STATES PATENT AND TRADEMARK OFFICE
CERTIFICATE OF CORRECTION

PATENT NO. : 5,098,396
DATED : March 24, 1992
INVENTOR(S) : Ellis R. Taylor et al.

It is certified that error appears in the above-identified patent and that said Letters Patent is hereby corrected as shown below:

Col. 1, line 7, change "Applicants" to --Applicants'--.

Col. 3, line 33, after "40" insert a period.

Claim 1, Col. 3, line 44, after "hub" insert --attached to the proximate end of said cannula;--

Signed and Sealed this

Seventh Day of February, 1995

BRUCE LEHMAN

Attest:

Attesting Officer

Commissioner of Patents and Trademarks